United States Patent
Magruder et al.

[11] Patent Number: 5,731,001
[45] Date of Patent: Mar. 24, 1998

[54] LOCKING COUPLINGS FOR OSMOTIC DELIVERY DEVICES

[76] Inventors: Judy A. Magruder, 355 Fay Way, Mountain View, Calif. 94043; James B. Eckenhoff, deceased, late of Los Altos, Calif. 94022; Bonnie J. Eckenhoff, 1080 Autumn Ln., Los Altos, Calif. 94022; Edward V. Bourneuf, 12132 Vivacite Walk, St. Louis, Mo. 63146; Richard Cortese, 20802 Laurel Rd., Los Gatos, Calif. 95030; Jeremy C. Wright, 631 Cuesta Dr., Los Altos, Calif. 94024; John R. Peery, P.O. Box 10362, Stanford, Calif. 94309; Ed Bourneuf, Vivacite Dr., St. Louis, Mo. 63146; James B. Pike, 223 Quailrun Dr., Defiance, Mo. 63141; Urano A. Robinson, 2163 Parasol Dr., Chesterfield, Mo. 63017; John M. Sharockman, 11518 Craig Ct., Creve Coeur, Mo. 63146; Jonathan P. Smith, 18636 Vixen Dr., Wildwood, Mo. 63069

[21] Appl. No.: 485,877

[22] Filed: Jun. 7, 1995

[51] Int. Cl.$^6$ ............................................. A61K 9/24
[52] U.S. Cl. ........................ 424/473; 424/438; 604/890.1
[58] Field of Search .............................. 424/473, 438; 604/890.1

[56] References Cited

U.S. PATENT DOCUMENTS

| | | | |
|---|---|---|---|
| 2,779,241 | 6/1957 | Howard | 89/1 |
| 3,845,761 | 11/1974 | Zaffaroni | 128/260 |
| 3,845,770 | 11/1974 | Theeuwes et al. | 128/260 |
| 3,865,108 | 2/1975 | Hartop | 128/260 |
| 3,882,233 | 5/1975 | Grant et al. | 514/21 |
| 3,896,819 | 7/1975 | Zaffaroni | 128/130 |
| 3,916,899 | 11/1975 | Theeuwes et al. | 128/260 |
| 3,987,790 | 10/1976 | Eckenhoff et al. | 128/260 |
| 3,995,631 | 12/1976 | Higuchi et al. | 128/260 |
| 3,995,632 | 12/1976 | Nakano et al. | 128/260 |
| 4,002,173 | 1/1977 | Manning et al. | 128/296 |
| 4,063,064 | 12/1977 | Saunders et al. | 219/121 |
| 4,077,407 | 3/1978 | Theeuwes et al. | 128/260 |
| 4,088,864 | 5/1978 | Theeuwes et al. | 219/121 |
| 4,111,202 | 9/1978 | Theeuwes et al. | 128/260 |
| 4,111,203 | 9/1978 | Theeuwes | 128/260 |
| 4,160,020 | 7/1979 | Ayer et al. | 424/15 |
| 4,179,337 | 12/1979 | Davis et al. | 424/78 |
| 4,200,098 | 4/1980 | Ayer et al. | 128/260 |
| 4,203,439 | 5/1980 | Theeuwes | 128/260 |
| 4,203,440 | 5/1980 | Theeuwes | 128/260 |
| 4,207,893 | 6/1980 | Michaels | 128/260 |
| 4,235,236 | 11/1980 | Theeuwes | 128/260 |
| 4,285,987 | 8/1981 | Ayer et al. | 427/3 |
| 4,309,996 | 1/1982 | Theeuwes | 128/260 |
| 4,320,759 | 3/1982 | Theeuwes | 128/260 |
| 4,327,725 | 5/1982 | Cortese et al. | 128/260 |
| 4,350,271 | 9/1982 | Eckenhoff et al. | 222/386 |
| 4,526,938 | 7/1985 | Churchill et al. | 525/415 |
| 4,599,229 | 7/1986 | Maccecchini | 424/85 |
| 4,612,008 | 9/1986 | Wong et al. | 604/892 |
| 4,612,186 | 9/1986 | Eckenhoff et al. | 424/15 |
| 4,643,731 | 2/1987 | Ekcenhoff | 604/892 |
| 4,652,630 | 3/1987 | Bentle et al. | 530/420.4 |
| 4,692,336 | 9/1987 | Eckenhoff et al. | 424/468 |
| 4,717,566 | 1/1988 | Eckenhoff et al. | 424/438 |
| 4,723,958 | 2/1988 | Pope et al. | 604/890.1 |
| 4,756,604 | 7/1988 | Nakatsuka et al. | 350/331 R |
| 4,765,980 | 8/1988 | Deprince et al. | 424/108 |

(List continued on next page.)

*Primary Examiner*—D. Gabrielle Phelan
*Attorney, Agent, or Firm*—Paul L. Sabatine; John A. Dhuey; Michael J. Rafa

[57] ABSTRACT

A delivery system is disclosed for delivering a fluid-sensitive active agent such as a somatotropin, or an analogue or derivative thereof, to an animal such as a bovine. The delivery system comprises a first wall section, a second wall section and a locking coupling therebetween. The coupled wall sections define a compartment, enclosing an active agent and an expandable driving member. Various embodiments of the locking coupling are disclosed.

7 Claims, 4 Drawing Sheets

U.S. PATENT DOCUMENTS

| | | | |
|---|---|---|---|
| 4,781,714 | 11/1988 | Eckenhoff et al. | 604/890 |
| 4,855,141 | 8/1989 | Eckenhoff et al. | 424/423 |
| 4,957,494 | 9/1990 | Wong et al. | 604/892.1 |
| 4,959,218 | 9/1990 | Eckenhoff et al. | 424/473 |
| 4,960,416 | 10/1990 | Stephens et al. | 604/892.1 |
| 4,963,141 | 10/1990 | Eckenhoff | 604/892.1 |
| 4,969,884 | 11/1990 | Yum | 604/892.1 |
| 4,976,966 | 12/1990 | Theeuwes et al. | 424/473 |
| 5,023,088 | 6/1991 | Wong et al. | 424/473 |
| 5,030,216 | 7/1991 | Theeuwes et al. | 604/892.1 |
| 5,037,420 | 8/1991 | Magruder et al. | 604/892.1 |
| 5,045,082 | 9/1991 | Ayer et al. | 604/892.1 |
| 5,057,321 | 10/1991 | Edgren et al. | 424/413 |
| 5,137,727 | 8/1992 | Eckenhoff | 424/422 |
| 5,238,687 | 8/1993 | Magruder | 424/473 |

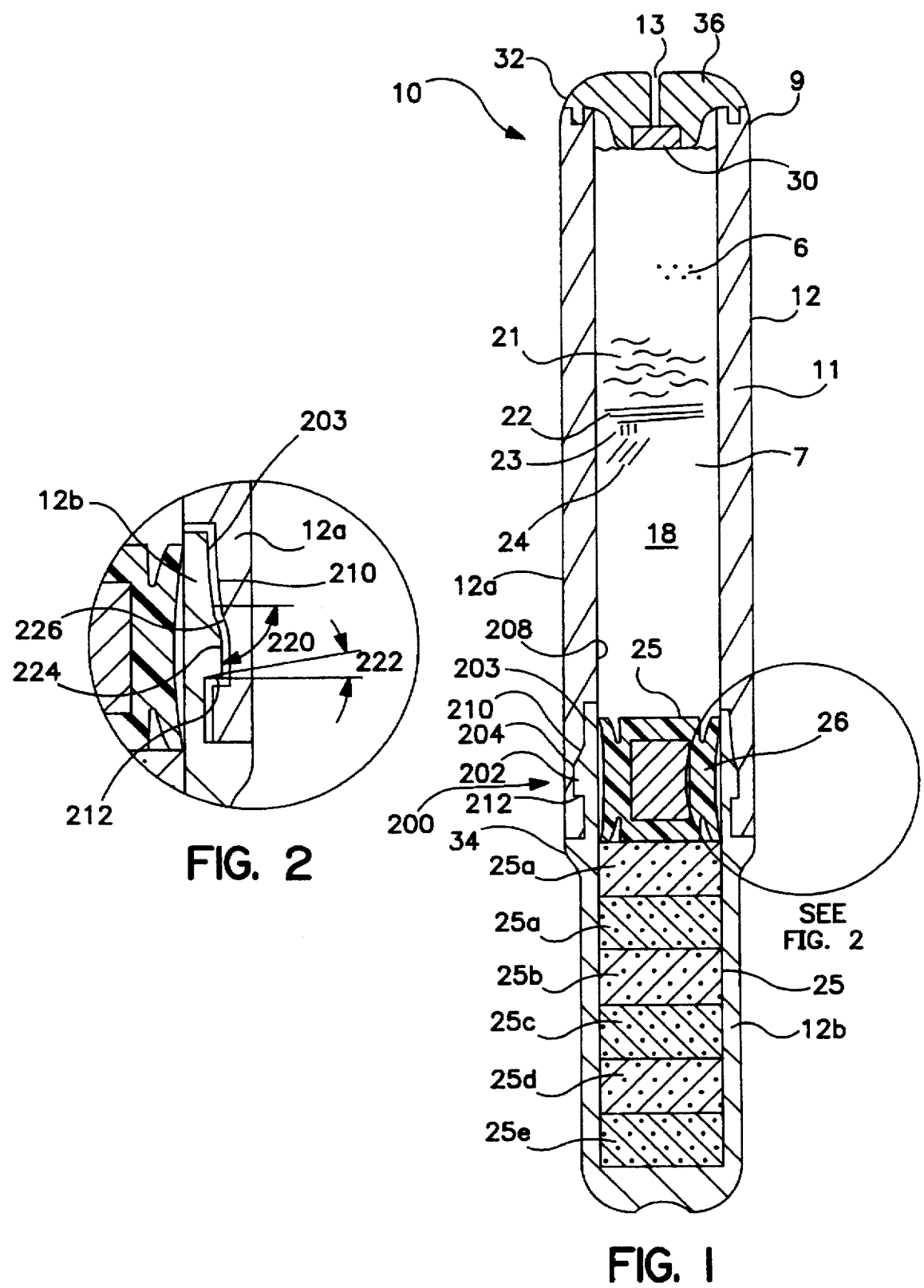

5,731,001

LOCKING COUPLINGS FOR OSMOTIC DELIVERY DEVICES

TECHNICAL FIELD

This invention pertains to both a novel and to an unobvious delivery system. Particularly, the invention relates to a delivery system that operates by osmosis and more particularly, the invention relates to a device that protects and administers a fluid-sensitive beneficial agent to a fluid environment.

BACKGROUND ART

Delivery devices for administering a beneficial agent to a biological, fluid environment of use are known to the prior art. See, for example, U.S. Pat. No. 5,137,727; U.S. Pat. Nos. 5,174,999; and 5,238,687.

These devices comprise a housing including fluid-impermeable first wall section and a fluid permeable second wall section. An active agent is enclosed within the first wall section. An expandable driving member is enclosed within the second wall section. A partition member is between the beneficial agent and the expandable driving member. An exit passageway is formed in the fluid impermeable first wall section. As fluid is imbibed through the fluid permeable second wall section, the driving member expands within the second wall section, pushing the partition member which forces the active agent through the exit passageway.

The delivery devices described in the above patents operate successfully for their intended use and they can deliver many beneficial agents for their intended effects. Now, it has been observed that their use can be limited because difficulties associated with shortening the start-up time for delivering the active agents from the device.

Implanted devices are continually exposed to biological fluids naturally present in the body. Fluids are imbibed across the fluid permeable wall sections containing the expandable driving member. When the partition layer or expandable driving member has occupied the entire volume defined within the first and second wall sections, the expandable driving member continues to expand. Pressure may accumulate within the device until it is sufficient to force a separation of the first wall section from the second wall section. Thus there is a need for a delivery device that is essentially free of the problems associated with the prior art and that, if such an implantable delivery device is provided, it would have a practical application in the fields of human and veterinary medicine particularly in the breeding and management of farm animals.

DISCLOSURE OF THE INVENTION

The present invention is directed to a fluid-imbibing delivery device or dispenser for storing and protecting a fluid-sensitive active agent and for dispensing the agent to a fluid environment of use over a prolonged period of time.

In accordance with another aspect of the present invention, a delivery device having a fluid permeable wall section and a fluid impermeable wall section includes a locking coupling between the fluid permeable wall section and the impermeable wall section to provide additional strength to the joint between the two wall sections.

In accordance with another aspect of this invention, a delivery device for storing and protecting an active agent and for dispensing the active agent to an environment of use includes a locking joint between the first and second wall portions of the delivery device. At least one of the wall sections has a mechanical rigidity greater than a wall section comprising 85% cellulose acetate butyrate and 15% tributylcitrate. A locking coupling between the first and second wall sections strengthens the joint between the two sections.

BRIEF DESCRIPTION OF THE DRAWINGS

In the drawing figures, which are not drawn to scale, but are set forth to illustrate various embodiments of the invention, the drawing figures are as follows:

FIG. 1 is a cross-sectional view of one embodiment of the delivery device of the invention, illustrating one structural embodiment of the delivery system comprising a first walled section and a second walled section.

FIG. 2 is an enlarged cross-sectional view of the locking coupling between the first wall section and the second wall section of taken from within the circle in FIG. 1.

DETAILED DESCRIPTION OF THE INVENTION

Figure 3:
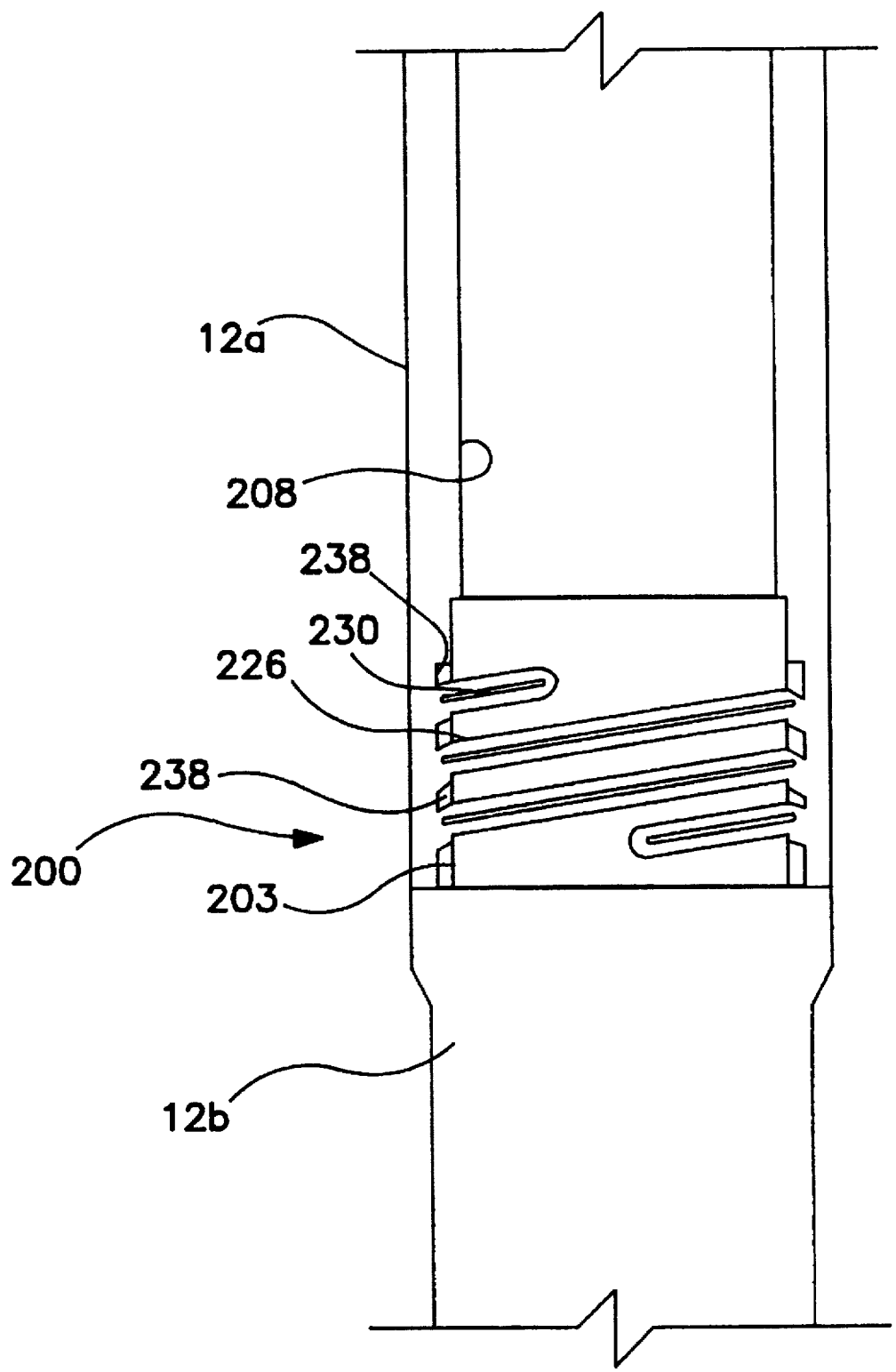
FIG. 3 is an enlarged cross-sectional view of another embodiment of the locking coupling of the FIG. 1.

In the following discussion, like reference numerals refer to like elements in the figures.

According to this invention, a locking coupling, as more fully described later in this application, strengthens the joint between the first and second wall sections. FIG. 1 illustrates one embodiment of the delivery device according to the present invention. Delivery system 10 of FIG. 1 comprises a housing 11 formed of a wall 12, which wall comprises a first wall section 12a and a second wall section 12b. Wall 12 encloses and defines an internal compartment 18. Delivery system 10 has at least one exit passageway 13 for delivering an active agent formulation 7 from delivery system 10.

Wall section 12a may be in the form of an tubular member having a first and a second open ends 32 and 34, respectively. In this particular embodiment, an end cap 36 is positioned on first wall section 12a at its lead end 9. Either the wall section 12a or end cap 36 define the passageway 13.

First wall section 12a encloses and defines the internal compartment 18 initially occupied by the active agent 7. First wall section 12a also comprises a composition that is substantially impermeable to the exchange of fluid, active agent 7 and other ingredients contained in delivery system 10. The phrase substantially impermeable, as used herein, indicates the volume of external fluid passing through the first wall section 12a is substantially negligible, that is, about zero up to about 1μ or up to about 1 ml/day. As a result, wall section 12a serves as a means for substantially protecting an active agent 7 that is sensitive to exterior fluid present in the environment of use. Other representative compositions for forming first section 12a such as vinylidene chloride copolymers and terpolymers acrylon; trile polymers, halogenated polymers and polycarbonates are discussed in U.S. Pat. No. 5,057,318, incorporated by reference herein.

Wall section 12b surrounds that portion of internal compartment 18 that contains expandable driving member 25 for expanding and for occupying space in compartment 18 for delivery of an active agent formulation from delivery system 10. Second wall section 12b is permeable to the passage of fluid and it is substantially impermeable to the passage of other ingredients contained in delivery system 10. The thickness and the surface area of the second wall section 12b contribute to the rate of passage of fluid through the membrane second wall section.

Typical semipermeable materials, flux enhancers and plasticizers for forming wall 12b are known in the art, and are described in detail in related application Ser. No. 08/269, 596, now U.S. Pat. No. 5,485,299 and in U.S. Pat. No. 5,057,318 already incorporated by reference.

If the material used in the formation of the wall section surrounding the osmotic driving member, for example wall section 12b, is not as strong as the material used in the formation of the portion surrounding the active agent 6, for example first wall section 12a, then the weaker material is preferably positioned or disposed to the inside or inserted within the stronger material. For example, if cellulose acetate butyrate is used for the portion surrounding the osmotic driving member and polypropylene is used to surround the active agent 7, then the cellulose acetate butyrate wall is preferably on the inside of the polypropylene wall.

Referring again to FIG. 1, compartment 18 comprises an active agent formulation 7, which active agent formulation 7 comprises an active agent 7a, identified by dots, and a pharmaceutically acceptable carrier 21, identified by wavy lines. The pharmaceutically acceptable carrier may include more than one ingredient, such as a buffer 22, identified by horizontal dashes; a pharmaceutically acceptable viscosity modulating vehicle 23, identified by vertical lines; a pharmaceutically acceptable surfactant 24, identified by slanted lines; and other formulation ingredients, as are known in the art. Delivery device 10 in its compartment 18 can also comprise pharmaceutical carrier 21. Carrier 21 may optionally include viscosity modulating vehicles (23), buffers (22), surfactants (24), dyes, and other additives known in the art, examples of which are disclosed in U.S. Pat. Nos. 5,034,229 and 5,135,123 to comprise the active agent formulation 7.

One class of fluid-sensitive agents that are presently preferred for delivery from the devices of the present invention are growth factors, including bovine somatotropin and analogues and derivatives thereof. The devices of the present invention provide a means for delivering an effective amount of an active agent for causing increased productivity, such as, in the case of the somatotropins, a higher feed conversion efficiency, improved carcass quality, higher than normal rate of animal weight gain, and increased milk production.

In a presently preferred embodiment, the active agent is bovine somatotropin, in an amount of from about 25% to about 60% by weight (wt. %) of the active agent formulation 7, preferably from about 30 wt. % to about 45 wt. %. In addition, a salt such as NaCl or KCl may be present in amounts of 1-4% by weight to assist stabilizing the state of formulation.

Wall section 12b surrounds, an expanding driving member 25 optionally comprising members 25a-f. Expandable driving member 25 expands in response to fluid imbibed across wall 12b and optionally comprises an osmagent homogeneously or heterogeneously blended with binder.

The expandable driving member 25, initially surrounded by second wall section 12b and operable for pushing the active agent formulation 20 from delivery device 10 comprises, in a presently preferred embodiment, an osmopolymer. The expandable driving member 25 in another preferred embodiment comprises an osmagent. The expandable driving member 25 yet in another preferred embodiment comprises an optional osmagent dispersed within the osmopolymer. Osmagents and osmopolymers are known to the art in U.S. Pat. Nos. 3,865,108, 4,002,173, 4,207,893, 4,327,725, 4,612,008, 5,034,229, and 5,135,123 for example, the disclosures of which are incorporated by reference herein.

In a presently preferred embodiment, delivery device 10 comprises a plurality of expandable driving members 25a-f initially housed in second wall section 12b. This configuration is merely illustrative and there may be any number of driving means present. Generally, there are from one to six expandable driving means; however, this number is not controlling. The expandable driving members in a presently preferred embodiment are formed as depots or layers and comprise like or unlike compositions. For example, driving means 25a-f can be made as tablets comprising like osmopolymers or like osmagents, or they can comprise unlike osmopolymers or unlike osmagents, or one or more of the members can be a composition comprising an osmopolymer together with an osmagent. The members can be the same or they can be different.

The terms "exit means" and "exit passageway", as used herein, comprise means and methods suitable for the metered release of the active agent 6 from compartment 18 of delivery device 10. This includes maintaining sufficient efflux or outward velocity of the active agent to prevent an inward flow of fluid from the external environment to dilute the active agent formulation in the portion of the compartment comprised by the first wall section. The exit passageway 13 includes at least one passageway, orifice, or the like, through first wall section 12a for communicating with compartment 18. The expression "at least one passageway" includes aperture, orifice, bore, pore, porous element through which the agent can migrate, hollow fiber, capillary tube, porous overlay, porous insert, and the like. The expression also includes material that gets discharged, erodes or is leached from the wall in the fluid environment of use to produce at least one passageway in delivery device 10. Passageways and materials, equipment and methods for forming passageways are disclosed in U.S. Pat. No. 5,034, 229.

Movable partition 26, positioned between the beneficial agent composition and the expandable driving member is a means for (1) maintaining the separate identity of the beneficial agent composition and the driving member, for (2) transmitting the force generated by the driving member against the beneficial agent composition, and (3) for substantially restricting the passage of fluid between the beneficial agent composition and the driving member. Representative materials include waxes, elastomeric pistons, and polymer compositions, examples of which are disclosed in U.S. Pat. No. 5,034,229 and related case U.S. Ser. No. 08/269,569, now U.S. Pat. No. 5,485,299.

In a preferred embodiment, the device 10 includes a delivery device characterized by a shortened start-up time, e.g., from 50 days to less than 21 days. It was discovered that as the fluid was imbibed through the semipermeable wall section 12b, rather than expanding longitudinally within the internal compartment 18 and forcing the active agent 7 out through the exit passageway 13, the expandable driving member 25 expanded, in part, radially outward. This extended the start-up time of the delivery device mby diverting the expansion radially outward, reducing the amount of longitudinal expansion and thus the push of the member 25 against the partition 26 or directly against the active agent 6. Responsive to this problem, to reduce the radial swelling of the semipermeable wall section, the rigidity of the wall was increased by reducing the amount of plasticizer in the wall composition. In one embodiment, to increase the wall's rigidity, the semipermeable wall section composition was comprised of 90% Cellulose acetate butyrate and 10% tributylcitrate. This compositional change had a significant effect on the semipermeable wall section strength, reducing the start-up time to less than 21 days by minimizing the radial swelling of the wall section.

As illustrated in FIGS. 1–6, a locking coupling 200 between the first and second wall sections provides a strengthened joint therebetween. The locking coupling is preferably used when the fluid permeable wall section is formed of material having a greater than or equal to the hoop strength or radial expansion of an 85% CAB and 15% TBC fluid permeable wall section composition. These embodiments are particularly useful in devices having shortened start-up times and are thus subjected to additional structural distress. For example, when the device has expelled all of the active agent formulation and the partition layer reaches the end cap, fluid continues to be drawn through the fluid permeable wall section and a build-up of pressure ensues within the device. The pressure will continue to build within the internal compartment 18. When the yield strength of the components is exceeded, the material failure of the device may occur. Those in the art will recognize various factors which contribute to the yield strength of a device include the materials used ( the differences between CAB/TBC ratios and the effect upon the materials characteristics), physical parameters such as thickness, area; and/or the expansion of the driving member. To adjust for this additional pressure, especially when 90/10 CAB/TBC wall formulations were utilized, wall sections 12a and 12b were configured to interlock mechanically with one another.

A preferred embodiment of the locking coupling 200 is illustrated in FIG. 1. In this embodiment, the locking coupling 200 is an annular snap joint which includes a coupling projection 202 formed on the outer surface 203 of second wall section 12b for receipt within annular joint depression 204 defined within the inside surface 208 of first wall section 12a. Coupling projection 202 has a gently sloped inserting face 210 and a sharply sloped, nearly perpendicular, retaining face 212.

As best shown in FIG. 2, a forward angle 220 is defined by the perpendicular to the outside surface 203 of the second wall section 12b and the surface of the inserting face 210. A large forward angle, i.e., a gentler slope, that is more parallel to the outside surface 203 of the second wall section 12b, will provide low resistance to insertion of the male telescoping second wall section 12b, into female first wall section 12a and into a mechanically engaged position. In one preferred embodiment, the forward angle 220 is 73°. A back angle 222 is defined by the perpendicular to the outside surface 203 of the second wall section 12b and the surface of the retaining face 212. A sharply sloping (more perpendicular to the longitudinal axis) back angle 222 resists withdraw of the male wall section 12b from engagement with the female wall section 12a and yields a stronger joint. A more gently sloped back angle 222 provides for a weaker joint, but requires less force to withdraw the wall section off the core pin after molding. A back angle between 10°–30° is easily molded and still gives a sufficiently strong joint. A 10°–20° is preferred and 15° back angle 222 is the most preferred since these angles provide inherently better joint strength characteristics. Still referring to FIG. 2, an adhesive receiving compartment 224 is defined between the first wall section 12a and the second wall section 12b, e.g., between the projection and the receiving depression, for receipt of an adhesive 226 therein. Representative adhesives include those that provide a strong mechanically and hydrostatically intact seal when they are bonded together, an adhesive, such as a pressure-sensitive contact adhesive, a moisture-curing adhesive, an ultraviolet-curing adhesive or the like are suitable for the purposes of this invention. Preferably the adhesive is a cyanoacrylate adhesive having a low-enough viscosity to wick into the joint and form a secure bond. A cyanoacrylate adhesive having the same qualities and characteristics as that sold by Loctite of Newington, Conn. under the brand name Loctite 4014 Prism Medical Grade.

The strength of the locking coupling of this embodiment is also a function of the depth of joint depression 204. Joint strength increases as the depression depth increase. The maximum depth is dependent upon the permissible strain of the second wall section material 12b. For example, the permissible strain for polypropylene is approximately 70% of its yield strength. To remain in the elastic region of the stress-strain curve for polypropylene, an undercut depth of 0.010 inches (0.0254 cm) provides sufficient joint strength without compromising the integrity of the material.

Another embodiment of the locking coupling 200 is shown in FIG. 3. In this embodiment the locking coupling is a screw joint, with the projection 230 preferably as a helically, outwardly extending threaded portion 226 of the second wall section 12b, formed on the outer surface 203 thereof. The projection 230 threadingly engages with a joint depression 238, for example, a threaded portion of the first wall section 12a. The helical receiving depression 238 is defined within the inside surface 208 of the female first wall section 12a for threaded engagement with the projection 230. The threaded portion of the first and second wall sections define a compartment 238 for receiving an adhesive therebetween. The width of the helical receiving groove is wider than the projecting threads to define helical adhesive receiving cavity 238. This provides additional strength to the joint. The adhesive is injected into the cavity before twisting and seating of the fluid permeable wall section 12b.

Figure 4:
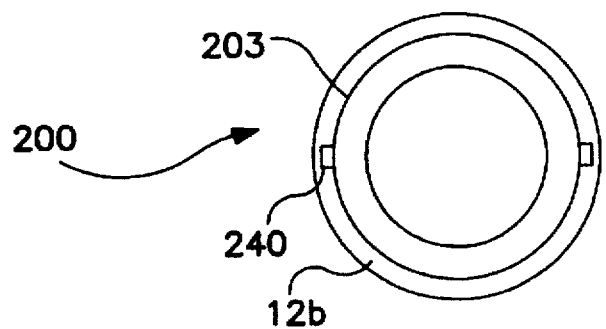
FIG. 4 is an enlarged top view of another embodiment of the locking coupling of FIG. 1, taken along the lines A—A of FIG. 5.
Figure 5:
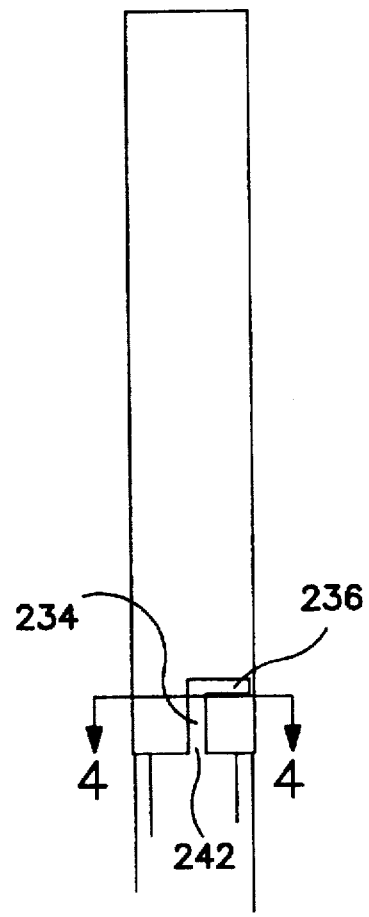
FIG. 5 is an enlarged, cross-sectional view of the still another embodiment of the locking coupling of FIG. 1.

As best shown in FIG. 4, another embodiment of the locking joint 200 is illustrated. In this embodiment, the locking joint is a bayonet joint which includes a projecting tab 240. Projecting tab 240 extends radially outward from the outside surface 203 of the male second wall section 12b. As shown in FIG. 5, receiving depression 242, sized to receive the projecting tab shown in FIG. 4, includes a first receiving portion 234 and a second receiving portion 236. First receiving portion 234 provides a means so that the projecting tab 240 is received within depression 242, when the male second wall section 12a telescopes longitudinally into the female first wall section 12b. Second receiving portion 236 is perpendicular to the first receiving portion 234 so that rotation of the inserted wall section about the longitudinal axis couples the wall sections.

Figure 6:
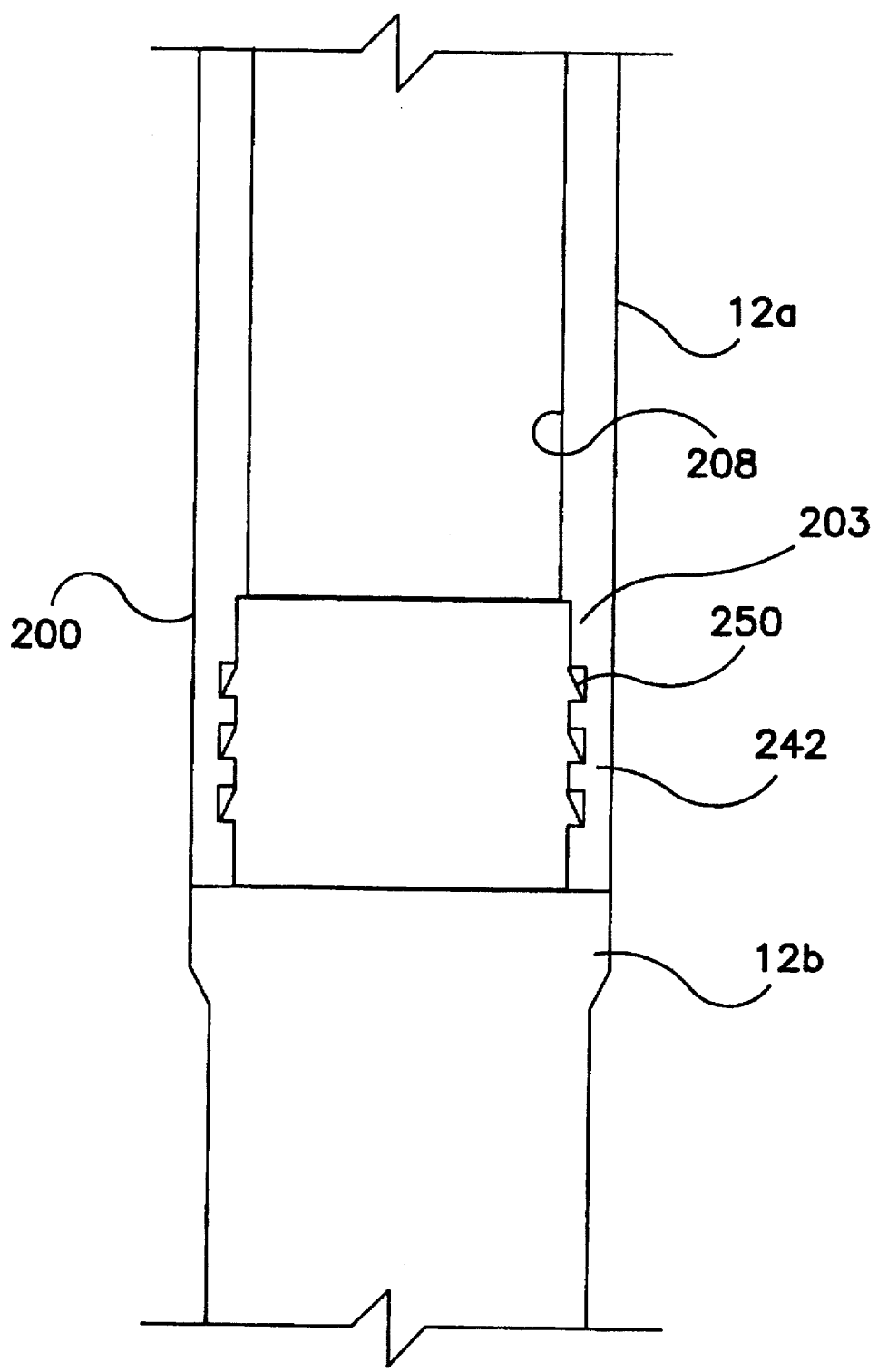
FIG. 6 is an enlarged, fragmented cross-sectional view of another embodiment of the locking coupling of FIG. 1.

Another embodiment of the locking joint 200 is illustrated in FIG. 6. In this embodiment, the locking joint 200 is a tabular snap fit joint. In this embodiment, a plurality of projections 250 extends outward from the outside surface 203 of second wall section 12b. The projection 250 is received within receiving depressions 242 defined within the inside surface 208 of the female first wall section 12a. This embodiment is similar to the annular snap joint embodiment of FIGS. 1 and 2 except that instead of an annular projection extending entirely around the outer surface 203 joint in this embodiment, the projections 250 and receiving depression 242 do not extend entirely about the circumference of the wall sections. In one preferred embodiment three tabs are equidistantly distributed about the circumference.

The implant can be implanted into the peritoneal cavity using an implanter. Generally, an implanter comprises a tubular member with a central longitudinal axial bore, a pointed, elongated, annular concavely beveled implanting end and an implant-charging end. The implanting end and the charging end communicate through a bore. A plunger adapted to be removably inserted in the bore is designed for slidable movement therein for applying the necessary force for implanting the implant. Alternatively, the implant can be surgically or subcutaneously implanted in the peritoneal cavity.

Delivery device 10 can be manufactured by standard manufacturing techniques. In one process, the first wall section 12a and the second wall section 12b are independently injection molded or extruded into the desired shape. Then, the first wall section 12a is filled with the active agent composition. The second wall section 12b is filled with an expandable driving member or members, and the piston 29 is next added thereto in layered arrangement. Optionally, the piston 29 may be added to the first wall section 12a after filling the wall section with active agent, in addition to, or instead of, the partition layer added to second wall section 12b. Next, the two sections at their open ends are slid together.

The delivery device of the present invention can be manufactured for delivering numerous active agents, including drugs, at a controlled rate to a presently preferred biological environment of use such as warm-blooded animals, including humans; ruminants, such as bovines and sheep; porcines, such as hogs and swine; horses; and the like. The delivery devices provide for high loading of an active agent and for its improved delivery in beneficially effective amounts (that is, amounts that provide a beneficial effect) over time. It is to be understood that the delivery devices can take a wide variety of shapes, sizes and forms adapted for delivering active agents to environments of use. For example, the devices manufactured as delivery devices can be used for dispensing an active agent in the anal-rectal passageway, in the cervical canal, as an artificial gland, in the vagina, as a subcutaneous or intraperitoneal implant, and the like. The delivery devices can be used in hospitals, nursing homes, outpatient clinics, sickrooms, veterinary clinics, farms, zoos, and other environments of use.

The following examples are merely illustrative of the present invention and they should not be considered as limiting the scope of the invention in any way, as these examples and other equivalents thereof will become apparent to those versed in the art in the light of the present disclosure, the drawings and the accompanying claims.

While there has been described and pointed out features of the invention as applied to presently preferred embodiments, those skilled in the art will appreciate that various modifications, changes, additions and omissions in the devices illustrated and described can be made without departing from the spirit of the invention.

What is claimed is:

1. An osmotic delivery device for dispensing an active agent to an environment of use, the delivery device comprising:

a first wall section;

a second wall section;

a mechanical interlock, said interlock comprising a coupling projection on one of said first and said second wall sections and a receiving depression in the other of said first and said second wall sections, between the first and second wall sections, the coupled sections defining an internal compartment;

an active agent and an expandable driving member enclosed within the compartment formed by the coupled first and second wall sections; and an exit passageway in the first wall section for delivering the active agent to the environment of use.

2. The device of claim 1, further comprising a movable partition between the active agent and the expandable driving member.

3. The device of claim 1, wherein the first wall section comprises a fluid impermeable material and the second wall section comprises an fluid permeable material.

4. The device of claim 1, wherein the projection and the depression define an adhesive receiving compartment therebetween.

5. The device of claim 1, wherein the projection comprises a threaded portion of the first wall section that threadingly engages with the depression that comprises a threaded portion of the second wall section.

6. The device of claim 5, wherein the threaded portion of the first and second wall sections define a compartment for receiving an adhesive therebetween.

7. The device of claim 1, wherein the projection comprises a gently sloping inserting face and a sharply sloping retaining face.

* * * * *